United States Patent [19]

Wong

[11] Patent Number: 4,883,966
[45] Date of Patent: Nov. 28, 1989

[54] PET CAMERA WITH CRYSTAL MASKING

[76] Inventor: Wai-Hoi Wong, 7903 Deer Meadow, Houston, Tex. 77071

[21] Appl. No.: 190,615

[22] Filed: May 5, 1988

[51] Int. Cl.⁴ .................................................. G01T 1/20
[52] U.S. Cl. ........................... 250/363.02; 250/363.09
[58] Field of Search .......... 250/363 SR, 368, 363 SD, 250/363.01, 363.02, 363.06, 363.09, 368

[56] References Cited

U.S. PATENT DOCUMENTS

| | | | |
|---|---|---|---|
| 4,092,540 | 5/1978 | Barrett | 250/363 SD |
| 4,514,632 | 4/1985 | Barrett | 250/363 SD |
| 4,563,582 | 1/1986 | Mullani | 250/363 S |
| 4,563,584 | 1/1986 | Hoffman et al. | 250/368 |
| 4,700,074 | 10/1987 | Basnjakovic | 250/363 S |
| 4,733,083 | 3/1988 | Wong | 250/363 S |
| 4,743,764 | 5/1988 | Casey et al. | 250/368 |

FOREIGN PATENT DOCUMENTS 1529215 10/1978 United Kingdom ................ 250/368

Primary Examiner—Janice A. Howell
Assistant Examiner—Richard Hanig
Attorney, Agent, or Firm—Fulbright & Jaworski

[57] ABSTRACT

A positron emission tomography camera having a plurality of crystals and planes which are positioned side-by-side and form adjacent rows of crystals transverse to the planes. Each row of each plane has a plurality of crystals and a row of light detectors are positioned adjacent each row of crystals. A row of reflecting masks are positioned between each row of crystals and each row of coacting light detectors and coded for providing an identification to the detectors of which crystal detects radiation. In addition, the ends of the crystals have a frosted finish and the sides have a polished finish for increasing the optical efficiency.

2 Claims, 3 Drawing Sheets

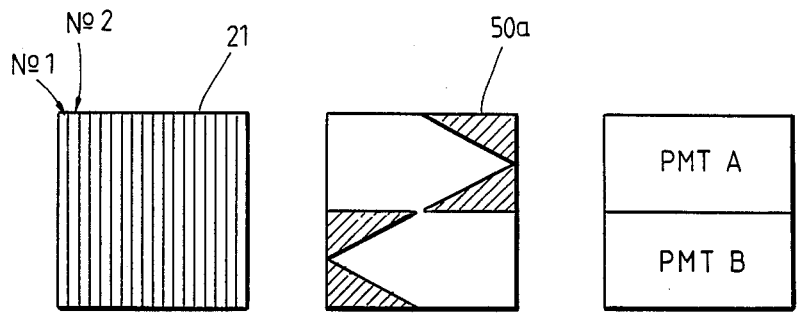
FIG.3a
(NARROW CRYSTALS)
FIG.3b
(REFLECTING MASK)
FIG.3c
(SQUARE DUAL PMT)
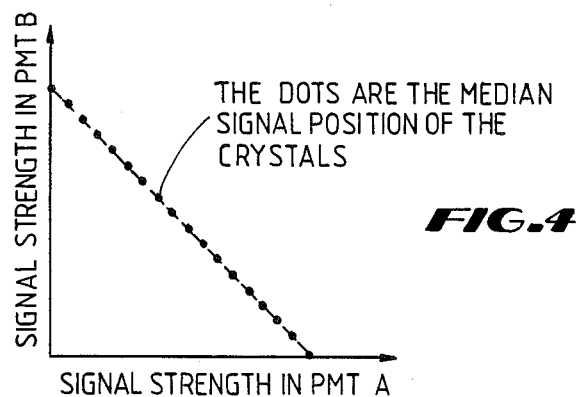
FIG.4
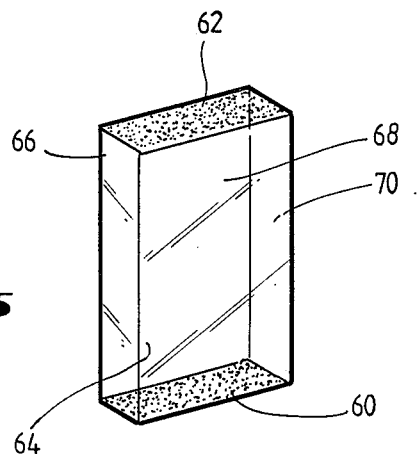
FIG.5

4,883,966

PET CAMERA WITH CRYSTAL MASKING

BACKGROUND OF THE INVENTION

The heart of a positron emission tomography camera (PET) is a set of gamma-ray detector rings surrounding the patient, such as disclosed in my U.S. Pat. No. 4,733,083. The detector rings consist of thousands of small scintillator detectors (crystals) closely packed together to form a ring without gaps in between. The scintillation light generated by the detector crystal on the detection of a gamma-ray is converted into electrical signal by a photomultiplier tube (PMT) optically coupled to each crystal. The highest image resolution achievable by any camera is equal to half the width of the scintillation crystal used in that camera. The crystal can be made very narrow (e.g. 1 mm), but the smallest available PMT is very big (10 mm). Hence, with the conventional crystal/PMT coupling, the best practically achievable image resolution for PET has been about 5 mm. In addition, with smaller detectors, the required number of crystal/PMT increases. The miniature PMTs are very expensive ($250 ea), and a typical high resolution PET requires 1500-2000 crystal/PMT channels. Hence the PMTs alone cost $500,000 plus additional affiliated signal processing electronics such as an amplifier per PMT, which is why PETs are expensive. Furthermore, the current commercial PETs, with their wider crystals, sample too coarsely in space that all the detectors are required to have a continuous scanning motion to improve the spatial data sampling. Moving 0.6-1.0 tons of the delicate detector system and keeping track of the instantaneous positions of all the detectors while each gamma-ray is being detected, is very costly mechanically and electronically.

The present invention aims to solve the three problems above:

(1) improving the ultimate PET image resolution with very narrow crystals without being restricted by the large size of the PMTs, so that image resolution of 2-3 mm can be achieved as compared to best current commercial camera resolution of 4.5-5 mm.

(2) decrease the number of PMTs and their affiliated electronics to 25% of the conventionally required number to greatly reduce the component cost.

(3) obviate the camera scanning motion by using very small detectors to improve the coarse spatial sampling problem to reduce the complexity and cost of the camera.

SUMMARY

The present invention is directed to a positron emission tomography camera having a plurality of scintillation crystals in planes which are positioned side-by-side around a patient area to detect radiation therefrom and forming adjacent rows of crystals transverse to the planes. Each row of each plane has a plurality of crystals for detecting radiation and a row of light detectors are positioned adjacent each row of crystals for receiving detected radiation from the adjacent row of crystals. A row of reflecting masks are positioned between each row of crystals and each row of coacting light detectors. The masks block the detected radiation from each crystal in each row a different amount for coding the output from the crystals and providing an identification to the light detectors of which crystal detects radiation.

Another object of the present invention is wherein the ends of the crystals have a frosted finish and the sides have a polished finish for increasing the optical efficiency.

Other and further objects, features and advantages will be apparent from the following description of presently preferred embodiments of the invention, given for the purpose of disclosure, and taken in conjunction with the accompanying drawings.

BRIEF DESCRIPTION OF THE DRAWINGS

FIG. 4 is a graph illustrating the light distribution mapping of the crystals, FIG. 5 is an enlarged perspective elevational view of a crystal with a hybrid surface finish used in the present invention, FIG. 6 are graphs illustrating the reflective light output of the present invention.

DESCRIPTION OF THE PREFERRED EMBODIMENTS

Figure 1:
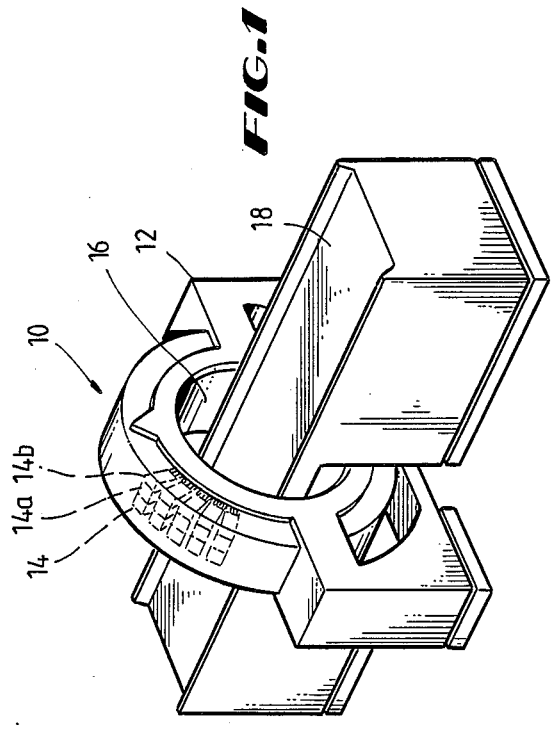
FIG. 1 is a perspective elevational view of a positron tomography camera of the present invention.

Referring to the drawings, and particularly to FIG. 1, the reference numeral 10 generally indicates a positron emission tomography (PET) camera having a support or gantry 12, a plurality of planes of detectors, here shown as rings, positioned side-by-side and surrounding a patient area 16 to detect radiation therefrom. The Patient area 16 may include a patient bed 18 for supporting a patient. In a PET camera, a positron isotope, such as Rb82, is injected into the patient and each positron isotope atom then produces two gammas simultaneously and back-to-back. The detectors then capture these gammas to produce an image of the tracer distribution.

Figure 2:
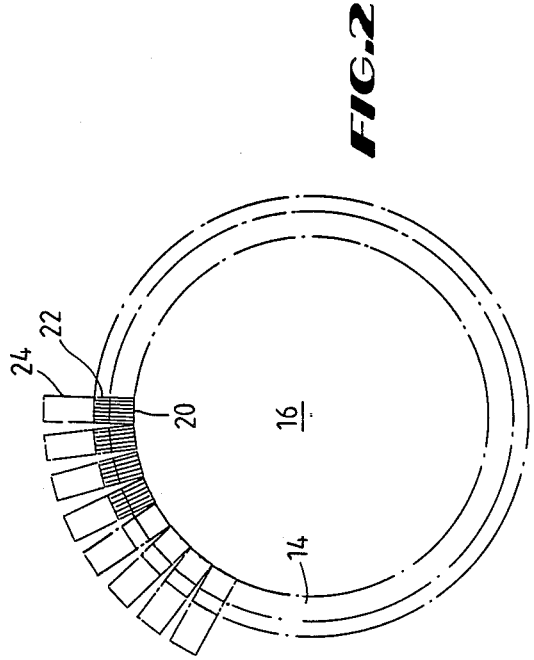
FIG. 2 is an enlarged schematic cross-sectional view of one ring or plane of crystals, mask, and light detectors around a patient area, FIGS. 3(a), (b), (c) illustrate the concept of coding of the present invention.

Each plane or ring, such as three p lanes 14, 14a and 14b, provides a straight on slice, and interplane slices between adjacent planes may be added together to provide an in-between slice between adjacent planes. Any desirable number of planes or rings 14 may be used. As best seen in FIG. 2, a single ring, such as 14, is illustrated and includes a plurality of scintillation crystals 20, a reflecting mask 22, and light detectors 24. The crystals may be of any suitable type, such as BGO crystals, and the light detectors 24 may be any suitable type, such as photomultiplier tubes or silicon avalanche photodiodes.

Figure 7:
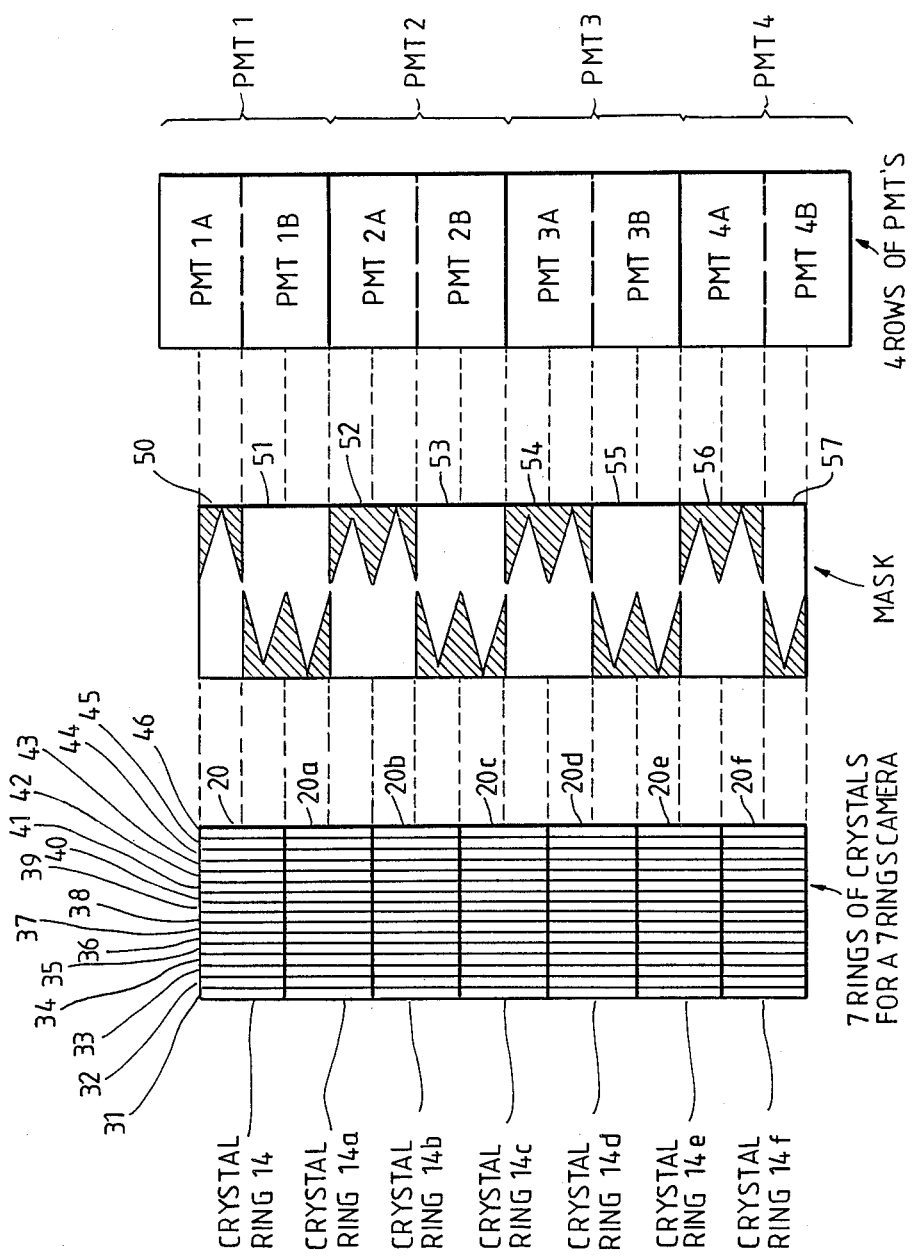
FIG. 7 is an alternate masking analog decoding design of the present invention.

Referring now to FIG. 7, a plurality of planes of scintillation crystals, here shown as seven rings 14, 14a, 14b, 14c, 14d, 14e, and 14f, include a plurality of sets of scintillation crystals generally indicated by the reference numerals 20, 20a, 20b, 20c, 20d, 20e, and 20f, positioned side-by-side around the patient area 16 to detect radiation therefrom and form adjacent rows of crystals transverse to said planes. That is, a plurality of crystal sets 20, 20a, 20b, 20c, 20d, 20e and 20f form a row transverse to the plane or rings 14-14f. Each row of each plane includes a plurality of crystals for detecting radiation. For example, in the plane 14, and in the single row consisting of sets 20-20f, sixteen crystals 31-45 may be provided in set 20. Similarly, sixteen crystals are provided in the same row of each of the sets of scintillation crystals 20a, 20b, 20c, 20d, 20e and 20f.

A row of light detectors are positioned adjacent each row of crystals for receiving detected radiation from the adjacent row of crystals and as shown in FIG. 7 the row includes photomultiplier tubes 1A, 1B, 2A, 2B, 3A, 3B, 4A, and 4B.

A row of masks is positioned between the row of crystal sets containing the crystal sets 20-20f and the row of detectors consisting of detectors 1A-4B. Thus a plurality of masks 50, 51, 52, 53, 54, 55, 56, and 57 are provided. The masks 50-57 are arranged for decoding the signals received from the crystals to provide an identification to the detectors of which crystal detects radiation. That is, mask 50 and half of mask 51 are designed to provide a different output to the PMTs 1A and 1B depending on which of the crystals 31-45 has been actuated.

Referring now to FIG. 3, the plurality of thin crystals are packed together in a small module (FIG. 3a) and a reflecting mask 50a (FIG. 3b) is placed between the set 21 of crystals and a square PMT unit made of two separate rectangular PMTs A and B (FIG. 3c). Thus, when crystal 1 detects a gamma-ray, only PMT A receives all of the scintillation light and PMT B receives no light. However, when crystal 2 detects a gamma-ray, PMT A receives a certain proportion of the light, depending upon the configuration of the mask 50a, such as 15/16 of the light while PMT B received 1/16 of the light. This analog logic continues for the rest of the crystals in the set 21. The light distribution mapping in FIG. 4 shows how the signal strength varies between PMT A and PMT B depending upon which of the crystals in the set 21 is actuated to provide a code or indication to the detectors of which crystal detects radiation.

The mask 50a will decrease the optical transmission of the light signal, which leads to a degradation of the signal integrity. However, with this mask design, the maximum light loss averages to 25% since the mask only blocks 25% of the total entrance window of the PMT geometrically. If the mask is made reflecting, any light blocked by the mask will be reflected back out again. The optical efficiency will be much higher.

A hybrid crystal surface finish is provided here to work with the reflecting mask 50a to maximize the light output. The hybrid finish is shown in FIG. 5, in which the PMT end 60 and the opposing end 62 have an etched or frosted finish whereas the four sides 64, 66, 68 and 70 have a highly polished finish. The hybrid finish invention utilizes the principles of (a) total internal reflection and (b) Lambert's directional diffusive reflection.

Figure 6A:
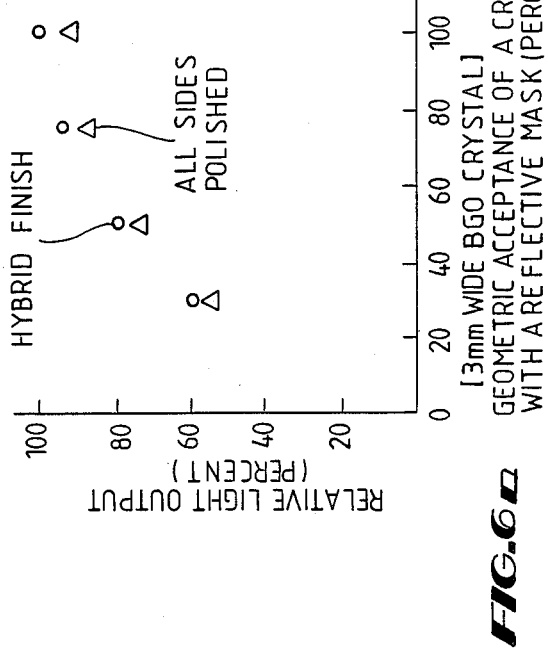
Figure 6B:
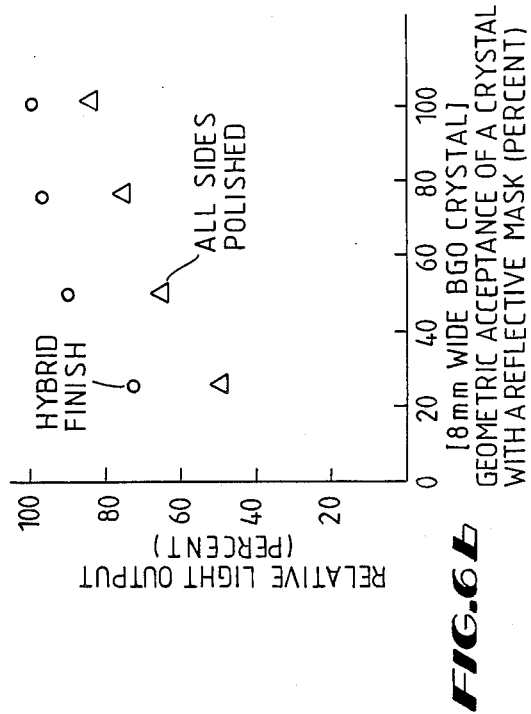

Preliminary measurements by the applicant, as indicated in the charts of FIG. 6, verify the superior optical transmission efficiency of the present design.

A 85-93% optical efficiency can be achieved depending on the width of the crystals. Hence the hybrid finish enhances the 75% geometrical efficiency of the mask significantly. The combined mask analog decoding scheme and a hybrid crystal finish create a new way for making high resolution camera without using a lot of ultra small PMTs (unavailable anyway). Using this scheme, a camera with 2-3 mm image resolution can be built with 2-3 mm wide crystal without any camera scanning movements.

FIG. 7 indicates an alternate masking analog decoding design with the same optical efficiency, but the slice resolution is only a quarter of the square PMT size. The tooth-shaped masks 50-57 are only schematic, that is, the edge of the teeth of the mask can be curved or in any other form to obtain the optimal separation in the decoding process.

The hybrid finish crystal as shown in FIG. 5 is also applicable for other crystal/PMT couplings because all PMTs have dead surface area which is not sensitive to light such as the glass wall of the tube and if the light incident on such dead areas are made to bounce back into the crystals and then bounce out again into the sensitive area to be detected, the light output efficiency will be higher. Another example is the use of circular PMTs coupling to the rectangular crystals. Part of the rectangular crystal cannot be covered by the circular PMT and light will be lost, unless the light is being reflected back and with the high reflection efficiency of the hybrid finish, this light will eventually come out to be detected by the circular PMT. Hence, the hybrid finish may be used for other crystal/PMT coupling schemes because of its high optical efficiency.

The present invention, therefore, is well adapted to carry out the objects and attain the ends and advantages mentioned as well as others inherent therein. While presently preferred embodiments of the invention have been given for the purpose of disclosure, numerous changes in the details of construction and arrangement of parts will be readily apparent to those skilled in the art and which are encompassed within the spirit of the invention and the scope of the appended claims.

What is claimed is:

1. A positron emission tomography camera comprising,
    a plurality of scintillation crystals in planes which are positioned side-by-side around a patient area to detect radiation therefrom and forming adjacent rows of crystals transverse to said planes,
    each row of each plane having a plurality of crystals for detecting radiation,
    a row of light detectors positioned adjacent each row of crystals for receiving detected radiation from the adjacent row of crystals,
    a row of reflecting masks positioned between each row of crystals and each row of coacting light detectors, said masks blocking the detected radiation from each crystal in each row a different amount for providing an identification to the light detectors of which crystal detects radiation.

2. The apparatus of claim 1 wherein the ends of said crystals have a frosted finish and said sides have a polished finish for increasing the optical efficiency.

* * * * *